United States Patent [19]

Lantzsch

[11] Patent Number: 4,897,505

[45] Date of Patent: Jan. 30, 1990

[54] PROCESS FOR THE PREPARATION OF 3-(2-CHLORO-2-(4-CHLORO-PHENYL)-VINYL)-2,2-DIMETHYLCYCLO-PROPANECARBOXYLIC ACID

[75] Inventor: Reinhard Lantzsch, Wuppertal, Fed. Rep. of Germany

[73] Assignee: Bayer Aktiengesellschaft, Leverkusen, Fed. Rep. of Germany

[21] Appl. No.: 290,216

[22] Filed: Dec. 27, 1988

[30] Foreign Application Priority Data

Jan. 5, 1988 [DE] Fed. Rep. of Germany ....... 3800097

[51] Int. Cl.$^4$ ............................................. C07C 61/40
[52] U.S. Cl. ................................................... 560/008
[58] Field of Search ......................................... 560/008

[56] References Cited

U.S. PATENT DOCUMENTS

| | | | |
|---|---|---|---|
| 4,157,397 | 6/1979 | Engel | 560/008 |
| 4,157,447 | 6/1979 | Engel | 560/008 |
| 4,160,842 | 7/1979 | Engel | 560/008 |
| 4,183,942 | 6/1980 | Engel | 560/008 |

FOREIGN PATENT DOCUMENTS 48370 3/1982 European Pat. Off. ................ 61/40
2916401 11/1980 Fed. Rep. of Germany .

OTHER PUBLICATIONS

Bhosale, S. S., Indian J. Chem., Sect. B, 24B(5), 543–546, 1985.
Lantzsch, R., Synthesis (11) 955–956, 1982.

*Primary Examiner*—Paul J. Killos
*Attorney, Agent, or Firm*—Sprung Horn Kramer & Woods

[57] ABSTRACT

3-(2-chloro-2-(4-chloro-phenyl)-vinyl)2,2-dimethylcyclopropanecarboxylic acid and its derivatives are obtained by reactive 3-chloro-3(4-chlorophenyl)-propenal with chloromethyl isopropyl ketone in a first step and reacting the resulting 4,4-dimethyl-1,3,6-trichloro-1-(4-chlorophenyl)-hex-1-en-5-one, optionally without isolation, in the presence of aqueous bases or in the presence of alkoxides. The resulting carboxylic acids or carboxylic acid esters can be converted into their derivatives such as, for example, salts, esters, amides or halides by generally known methods.

1 Claim, No Drawings

PROCESS FOR THE PREPARATION OF 3-(2-CHLORO-2-(4-CHLORO-PHENYL)-VINYL)-2,2-DIMETHYLCYCLOPROPANECARBOXYLIC ACID

The present invention relates to a new process for the preparation of 3-(2-chloro-2-(4-chlorophenyl)-vinyl)-2,2-dimethylcyclopropanecarboxylic acid.

It has been disclosed that this carboxylic acid can be prepared by reaction of 3-chloro-3-(4-chlorophenyl)-propenal with methyl isopropyl ketone, bromination of the resulting 4,4-dimethyl-1,3-dichloro-1-(4-chlorophenyl)-hex-1-en-5-one with bromine and subsequent cyclization with ring contraction in the presence of aqueous liquors (EP-OS 95,047). However, the economy of this reaction sequence is not completely satisfactory.

It has now been found that 3-(2-chloro-2-(4-chlorophenyl)-vinyl)-2,2-dimethylcyclopropanecarboxylic acid and its derivatives are obtained by reacting 3-chloro-3-(4-chlorophenyl)-propenal with chloromethyl isopropyl ketone in a first step and reacting the resulting 4,4-dimethyl-1,3,6-trichloro-1-(4-chlorophenyl)-hex-1-en-5-one, optionally without isolation, in the presence of aqueous bases or in the presence of alkoxides.

The resulting carboxylic acids or carboxylic acid esters can be converted into their derivatives such as, for example, salts, esters, amides or halides by generally known methods.

By conducting the reaction in this manner, the carboxylic acids can be obtained in substantially better yields than by the known methods. In order to be able to make a meaningful comparison of the yields, the following processes must be summarized and compared:

I. known
(a) 3-Chloro-3-(4-chlorophenyl)-propenal reacted with methyl isopropyl ketone, yield according to EP-OS 95,047 Example 1 = 72.7%
(b) 4,4-Dimethyl-1,3-dichloro-(4-chlorophenyl)-hex-1-en-5-one reacted with bromine, yield according to EP-OS 95,047 Example 2 (reworking) = 75%
(c) 4,4-Dimethyl-1,3-dichloro-6-bromo-(4-chlorophenyl)-hex-1-en-5-one reacted with aqueous alkali, yield according to EP-OS 95,047 Example 3 (reworking) = 82%

Total yield of the reactions a+b+c = 44.7%.

II. comparison
(a) 3-Chloro-3-(4-chlorophenyl)-propenal reacted with methyl isopropyl ketone, yield according to EP-OS 95,047 Example 1 = 72.7%
(b) 4,4-Dimethyl-1,3-dichloro-(4-chlorophenyl)-hex-1-en-5-one reacted with chlorine, yield = 60.2% (this example is not described in the prior art)
(c) 4,4-Dimethyl-1,3,6-trichloro-1-(4-chlorophenyl)-hex-1-en-5-one reacted with aqueous alkali, yield = 94% (this example is not described in the prior art)

Total yield of the reactions a+b+c = 41.1%.

II. according to the invention
(a) Methyl isopropyl ketone reacted with chlorine, yield = 78%
(b) 3-Chloro-3-(4-chorophenyl)-propenal reacted with chloromethyl isopropyl ketone, yield = 92%
(c) 4,4-Dimethyl-1,3,6-trichloro-1-(4-chlorophenyl)-hex-1-en-5-one reacted with aqueous alkali, yield = 94%

Total yield of the reactions a+b+c+ 67.5%.

By conducting the reaction according to the invention, an increase in the total yield of desired carboxylic acid from 41.1 or 44.7 to 67.5% is achieved. It was particularly surprising that the desired product could be obtained in such high yields in the reactions according to the invention.

The starting materials employed for carrying out the reactions according to the invention are known. The first step of the reaction according to the invention can be carried out with or without diluents. The starting materials are employed in approximately equimolar proportions. An excess of up to 4 equivalents of chloromethyl isopropyl ketone, relative to the 3-chloro-3-(4-chlorophenyl)-propenal, is particularly advantageous when working without diluents.

Suitable diluents are: hydrocarbons such as cyclohexane, petroleum ether, benzene or toluene, chlorinated hydrocarbons such as dichloromethane, chloroform, carbon tetrachloride or chloroenzenes, ethers such as diethyl ether, diisopropyl ether, methyl t-butyl ether, tetrahydrofuran, dioxane or 1,2-dimethoxyethane, and aliphatic acids such as acetic acid or propionic acid.

The reaction is carried out in the presence of at least equimolar amounts of hydrogen chloride. An excess of up to 4 moles can be advantageous.

The reaction is carried out at temperatures between $-20°$ C. and $+30°$ C., preferably between $0°$ C. and $+20°$ C.

The reaction can be carried out at atmospheric pressure or elevated pressure.

For working up, solvent, excess chloromethyl isopropyl ketone and hydrogen chloride are removed by distillation. The product thus obtained can be employed in the next step without further purification.

In the second step, the 4,4-dimethyl-1,3,6-trichloro-1-(4-chlorophenyl)-hex-1-en-5-one obtained in the first step is reacted in a diluent with an aqueous base or with alkoxides.

Suitable diluents are: alcohols such as methanol, ethanol or t-butanol. Suitable bases are: aqueous alkali such as sodium hydroxide solution or potassium hydroxide solution. Suitable alkoxides are: sodium alkoxides or potassium alkoxides such as ethoxides or methoxides.

The base is advantageously employed in an excess of 2 to 10 equivalents per equivalent of 4,4-dimethyl-1,3,6-trichloro-1-(4-chlorophenyl)-hex-1-en-5-one. The reaction temperature can be varied within a relatively wide range. Customarily, the reaction is carried out at room temperature.

The working up of the reaction mixture takes place in a customary manner by neutralization, removal of the solvent by distillation in vacuo, extraction of the resulting ester or release of the resulting acid by acidification using mineral acids and subsequent extraction.

EXAMPLE 1 (first step of the reaction according to the invention)

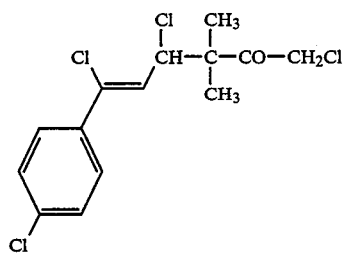

20.1 g (0.1 mol) of Z-3-chloro-3-(4-chlorophenyl)-propenal and 36.2 g of 1-chloro-3-methyl-butan-2-one (93% pure=0.28 mol) are initially introduced and hydrogen chloride is introduced for 5 minutes at 10° to 15° C. with stirring. The reaction is stirred for a further 12 hours at 20° C.

The excess chloromethylbutanone is subsequently distilled off at 100° C. bath temperature/80 mbar.

The residue is freed from low-boiling secondary components at 60° C./0.1 mbar and can be directly reacted further: 36.4 g; purity: 86%=92% of theory. By the addition of a little methanol, 25.8 g of yellow crystals of melting point 72° to 74° C. are obtained.

EXAMPLE 2 (second step of the reaction according to the invention)

10 g (0.11 mol) of 45% strength sodium hydroxide solution are added dropwise at 20° to 25° C. during the course of 30 minutes to a suspension of 7 g (0.02 mol) of 4,4-di-methyl-1,3-dichloro-6-chloro-1-(4-chlorophenyl)-hex-1-en-5-one in 20 ml of methanol. The reaction is subsequently stirred for 3 hours at 35° to 40° C. After neutralization using concentrated hydrochloric acid, the main amount of methanol is removed by evaporation in vacuo. The solution remaining is adjusted to pH 3 using concentrated hydrochloric acid, extracted using toluene at 40° C. and the solvent is stripped off. 5.36 g (94% of theory) of cis/trans-3-(Z-2-chloro-2-(4-chlorophenyl)-vinyl-2,2-dimethylcyclopropanecarboxylic acid are obtained.

EXAMPLE A (preparation of the starting material)

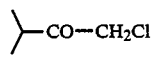

86 g (1 mol) of methyl isopropyl ketone and 200 ml of methanol are initially introduced. Hydrogen chloride (about 4 g) is then introduced with cooling (strongly exothermic).

Subsequently, 71 g (1 mol) of chlorine is introduced at −5° C. to −10° C. After stirring for 10 minutes, the mixture of methanol and hydrogen chloride is removed by distillation at 25° C./40 mbar (it can be used for the next batch).

The residue weighs 169.5 g and is fractionated through a 30 cm column in vacuo. 94 g of 1-chloro-3-methyl-butan-2-one of boiling point 73° to 75° C./64 mbar are obtained. This corresponds to a yield of 78% of theory.

EXAMPLE (B) (comparison)

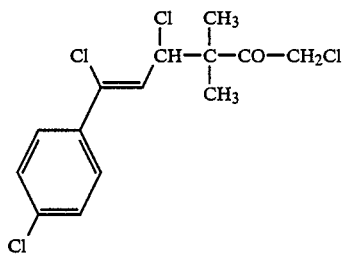

15.3 g (0.05 mol) of 4,4-dimethyl-1,3-dichloro-1-(4-chlorophenyl)-hexen-5-one are dissolved in 50 ml of acetic acid which contains some hydrogen chloride. 3.6 g of chlorine (0.05 mol) are introduced at 15° C. with good stirring. The mixture is stirred for one hour at about 15° C. and concentrated on a vapour diffusion pump.

13.2 g of a product mixture which consists to 77.5% of 4,4-dimethyl-1,3,6-trichloro-1-(4-chlorophenyl)-hex-1-en-5-one are obtained. This corresponds to a yield of 60.2% of theory.

What is claimed is:

1. A process for the preparation of 3-(2-chloro-2-(4-chlorophenyl)-vinyl)-2,2-dimethylcyclopropanecarboxylic acid or esters or derivatives thereof comprising reacting in a first step 3-chloro-3-(4-chlorophenyl)-propenal with chloromethyl isopropyl ketone to form 4,4-dimethyl-1,3,6-trichloro-1-(4-chlorophenyl)-hex-1-en-5-one and in a second step reacting said hex-1-ene-5-one, with or without isolation thereof from the first reaction, in the presence of aqueous base or in the presence of alkoxide to yield the acid or its ester.

* * * * *